United States Patent [19]

Kunzel et al.

[11] 3,932,409

[45] Jan. 13, 1976

[54] URETHANE DERIVATIVES OF 2-PHENYL-4(3H)-QUINAZOLONES

[75] Inventors: Hans-Egon Kunzel; Gerhard Dieter Wolf, both of Dormagen; Robert Bierling, Wuppertal-Elberfeld; Siegfried Petersen, Leverkusen; Gunther Nischk, Dormagen; Dieter Steinhoff, Bochum, all of Germany

[73] Assignee: Bayer Aktiengesellschaft, Germany

[22] Filed: June 7, 1974

[21] Appl. No.: 477,442

Related U.S. Application Data

[63] Continuation-in-part of Ser. No. 188,454, Oct. 12, 1971, abandoned.

[52] U.S. Cl..... 260/256.4 Q; 260/256.5 R; 424/251
[51] Int. Cl.$^2$................................... C07D 239/00
[58] Field of Search............ 260/256.4 Q, 256.5 R

[56] References Cited

UNITED STATES PATENTS

3,448,109   6/1969   Heusner et al.................. 260/256.4

*Primary Examiner*—Leonard Schenkman

[57] ABSTRACT

2-Phenyl-4(3H)-quinazolones bearing a urethane or thiourethane group on the 2-phenyl substituent, a second urethane or thiourethane group on the benzo ring of the quinazolone nucleus and an alkyl, cycloalkyl or phenyl group in the 3-position are prepared by treating the corresponding bis-amino compound with an acid derivative or the corresponding bis(isocyanate) or bis(isothiocyanate) with an alcohol. The compounds, of which 2-[3'-(methoxycarbonylamino)-phenyl]-3-phenyl-6-methoxycarbonylamino-4-(3H)-quinazolone is a typical embodiment, are cytostatic agents.

23 Claims, No Drawings

URETHANE DERIVATIVES OF 2-PHENYL-4(3H)-QUINAZOLONES

This is a continuation-in-part of our copending application Ser. No. 188,454 filed Oct. 12, 1971, now abandoned.

The present invention relates to new quinazolonediurethanes, to processes for their production and medicinal use as cytostatic agents.

Some quinazolone derivatives having hypnotic, tranquillizing and/or muscle-relaxing properties are known. See e.g., Angew. Chemie 74 (1962), 855–861. None of these derivatives are known to have any effect against malignant growth.

The present invention provides a new class of quinazolone derivatives of the formula:

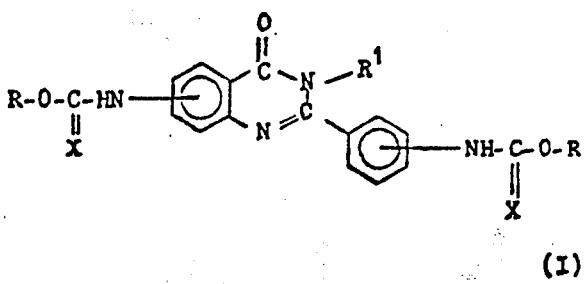

(I)

in which
X is an oxygen or sulfur atom;
R is an optionally substituted alkyl radical optionally having its carbon chain interrupted by an oxygen or sulfur atom; or an optionally substituted cycloalkyl radical, aralkyl or aryl radical; and
$R^1$ is an optionally substituted alkyl, cycloalkyl or phenyl radical.

A preferred class of the above compounds are those of the formula:

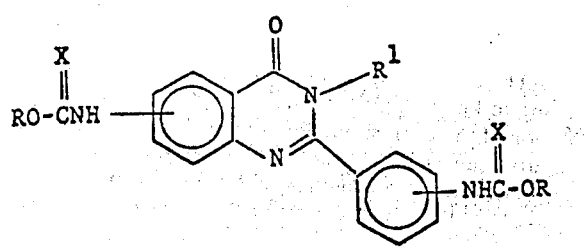

wherein
X is oxygen or sulfur;
$R^1$ is lower alkyl, cycloalkyl, unsubstituted phenyl or phenyl substituted with from one to three members selected from the group consisting of chloro, fluoro, bromo, lower alkyl or lower alkoxy; and
R is cycloalkyl, (lower alkyl)cycloalkyl, unsubstituted alkyl or lower alkyl substituted by hydroxy, lower alkoxy, phenyl, phenoxy, cycloalkyl, furyl, tetrahydrofuryl, imidazolyl, triazole or -$NR^2R^3$ wherein $R^2$ and $R^3$ when taken independently are lower alkyl and when taken together are alkylene of from four to seven carbon atoms.

By the term alkyl is intended a straight or branched monovalent hydrocarbon chain of from one to 20 carbon atoms. When qualified by the term "lower," such chains will contain from one to six, preferably one to four, carbon atoms. Typical of such groups are thus methyl, ethyl, propyl, isopropyl, butyl, sec.-butyl, isobutyl, tert.butyl, pentyl, neopentyl, hexyl and the like. The term lower alkoxy refers to a lower alkyl group joined to the remainder of the molecule through an ethereal oxygen atom, such as methoxy, ethoxy, propoxy, isopropoxy, butoxy and the like. Cycloalkyl denotes a monovalent saturated cyclic hydrocarbon group of from three to seven, preferably five or six, carbon atoms such as cyclopropyl, cyclobutyl, cyclohexyl and cycloheptyl.

Thus in the compounds of the present invention, the substituent $R^1$ can be a straight-chain or branched alkyl radical with one to 20, especially with one to four, carbon atoms, a cycloalkyl radical of three to seven, especially five or six, carbon atoms, or a phenyl radical which can be unsubstituted or can carry one or more, preferably one to three, substituents. Preferred substituents are halogen atoms, especially fluorine, chlorine and bromine, lower alkyl, especially methyl or ethyl, and lower alkoxy.

The substituent R can similarly be a cycloalkyl group of three to seven, especially five or six, carbon atoms or a straight-chain or branched alkyl radical with one to 20, especially one to six, carbon atoms, i.e., lower alkyl. When R is lower alkyl, it can be unsubstituted or can carry one or more, preferably one or two, substituents such as halogen atoms, especially fluorine, chlorine and bromine, cyano, hydroxy, carboxyl, carbo(lower alkoxy), sulfonic acid, lower alkoxy, phenyl, phenoxy, diloweralkylamino, saturated five to seven -membered heterocyclic ring, or a heterocyclic ring such as furyl, tetrahydrofuryl, imidazolyl or triazolyl.

The invention further provides processes, hereinafter designated (a) and (b), for the production of these new quinazolone derivatives.

Process (a) comprises reacting a diamine of the formula:

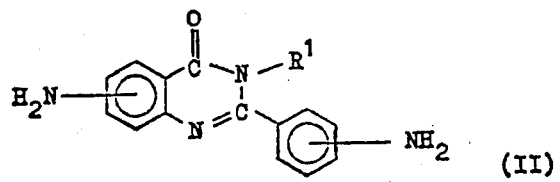

(II)

with an acid derivative of the formula:

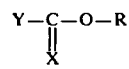  (III)

in which R, R¹ and X are as defined above, and Y is a halogen atom, preferably a chloro, bromo, or lower alkoxy, OCOlower alkoxy, or —S.CH₂.CO.OH.

Process (b) comprises reacting a diisocyanate or dithioisocyanate of the formula:

 (IV)

with an alcohol of the formula:

RGH  (V)

in which R, R¹ and X are as defined above.

Taking 2-(3'-aminophenyl)-3-phenyl-6-amino-4-(3H)-quinazolone and chloroformic acid methyl ester as typical starting materials, the course of the reaction in Process (a) can be represented in the specific following equation:

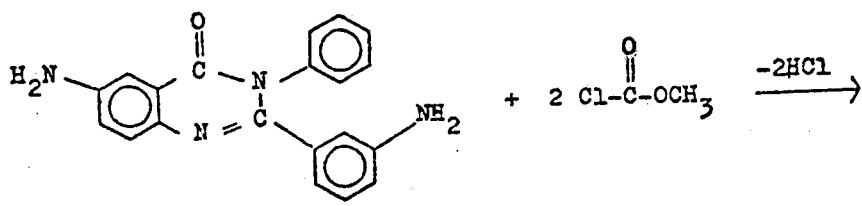

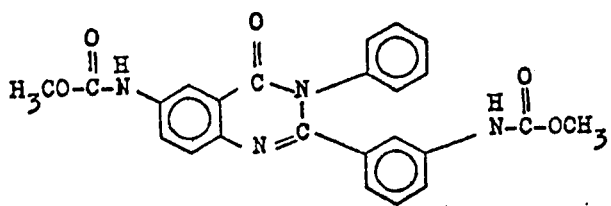

Taking 2-(3'-isocyanatophenyl)-3-phenyl-6-isocyanato-4-(3H)-quinazolone and methanol as typical starting materials, the course of the reaction in Process (b) can be represented in the specific following equation:

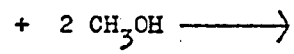

+ 2 CH₃OH ⟶

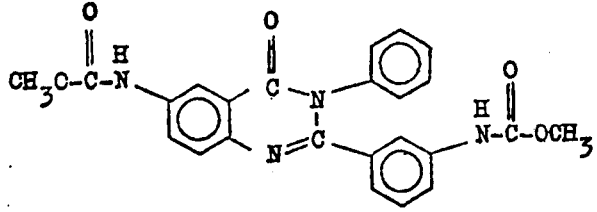

The diamines of formula (II) can be obtained according to known methods such as by catalytic hydrogenation of the corresponding dinitro compounds, which, in turn, can be produced from nitroanthranilic acids and N-substituted nitrobenzimide chlorides in a polar solvent such as acetone and in the presence of an aliphatic tertiary amine such as triethylamine at a temperature between 0° and 50°C. (see German Offenlegungsschriften Nos. 1,809,174 and 1,809,175). Alternatively, the dinitro compounds can be produced by reaction of nitroanthranilic acids and nitrobenzoyl chlorides to give the corresponding benzoxazinones which are then reacted with primary aliphatic or aromatic amines. In both cases, intermediate products which are sometimes first produced can be cyclized either thermally by heating above 100°C. in an organic solvent such as glycerol or with a dehydrating agent such as phosphorus pentoxide in N-methylpyrrolidone to yield the dinitro compounds.

The diisocyanate of formula (V) used in Process (b) can be produced from a diamine of formula (II) as for example by phosgenation of the hydrochloride in chlorobenzene at 80° to 120°C.

The dithioisocyanates of formula (IV) used in Process (b) according to the invention can be prepared from the corresponding diamines of formula (II) by reaction with thiophosgene, for example at 15° to 35°C., in the presence of calcium carbonate in aqueous suspension. β-Hydroxyurethanes of formula (I) can be obtained from the diamines by reaction with glycol carbonates.

The acid derivatives of formula (III) used in Process (a) and the alcohols ROH used in Process (b) are known.

As a diluent in Process (a) there can be used any solvent which does not react with compounds of the general formulas (II) and (III). Preferably, however, solvents in which both the starting compounds and the end product are easily soluble are used, as for example, aliphatic ketones, such as acetone, aromatic hydrocarbons, such as benzene or toluene, and chlorinated hydrocarbons, such as chlorobenzene. Preferably however an N,N-dialkylamide of a lower alkanoic acid such as dimethylformamide or dimethylacetamide and an N-alkyllactam such as N-methylpyrrolidone is used as solvent.

An excess of the alcohol ROH is preferably used as the solvent for the process (b); however, the reaction can also be carried out in the presence of an inert diluent, for example, dioxane, aromatic hydrocarbons, dimethylformamide, dimethylacetamide and N-methylpyrrolidone.

Any of the customary acid-binding agents can be used to bind the acid liberated in Process (a).

In those cases in Process (a) in which the solvent itself does not act as an acid acceptor, it is advisable to bind the hydrochloric acid produced with an inorganic or organic base as for example an alkaline earth metal or alkali metal carbonate or hydroxide or tertiary amine. Examples of such acid binding agents are sodium hydroxide, potassium carbonate, calcium carbonate, sodium bicarbonate, triethylamine and pyridine.

In Process (a), the temperature at which the compounds of formulas (II) and (III) are reacted can be varied over a substantial range, in general from about −10° to about 100°C., preferably between 0° and 50°C.

The temperature at which the compound of formula (IV) and the alcohol ROH are reacted in Process (b) can also be varied over a substantial range, in general from about 10° to about 120°C., preferably between 25° and 80°C.

In Process (a), at least 2 mols of the acid derivative of formula (III) are employed per mol of the diamine of formula (II); most preferably the molar ratio diamine: acid is from 1 : 2.1 to 1 : 3.

The reaction of the diamine of formula (II) with the acid derivative of formula (III) in Process (a) can be carried out not only in solution but also, if desired, in suspension or in emulsion, for example in water. In these cases, however, it is advisable to employ a larger excess of the acid derivative (III).

In Process (b), preferably 1 to 10 mols, especially 2.2 to 6 mols, of the alcohol ROH are employed per mol of the compound of formula (IV), unless the alcohol is used as the solvent.

When the alcohol ROH is reacted with the diisocyanate or diisothiocyanate of formula (IV) in Process (b) it is advisable to add a small amount of a basic catalyst, for example triethylamine, pyridine, triethylenediamine or dimethylcyclohexylamine. This catalyst is generally added in an amount of 0.1 to 5 per cent by weight, relative to the amount by weight of the total reaction mixture.

Table 1 sets forth a number of typical quinazolonediurethanes of the invention as illustration of the compounds within its scope.

Table 1

Compound No.  Formula (1)

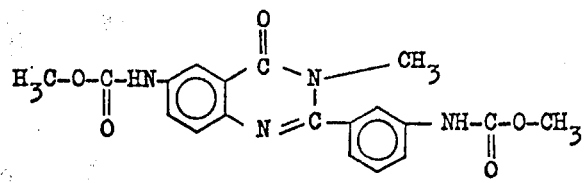

(2)

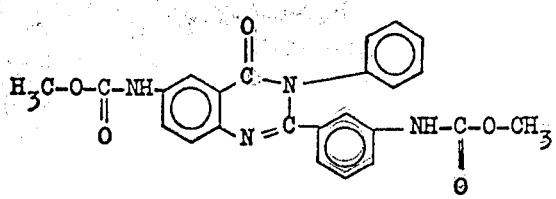

Table 1 (cont'd)
Compound No.          Formula
(3)
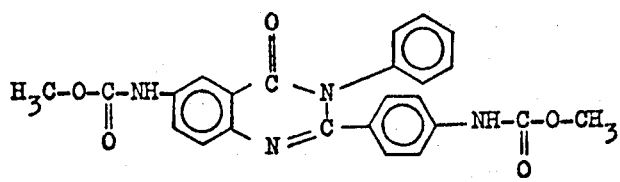
(4)
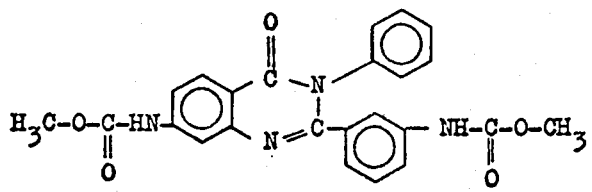
(5)
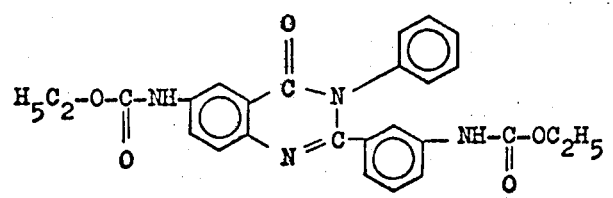
(6)
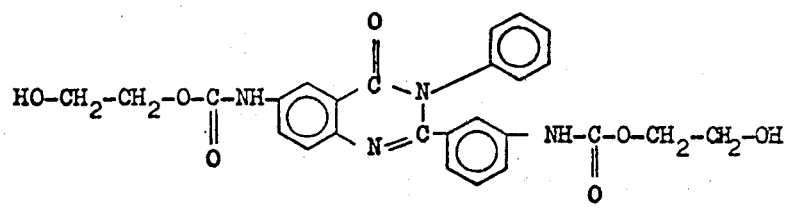
(7)
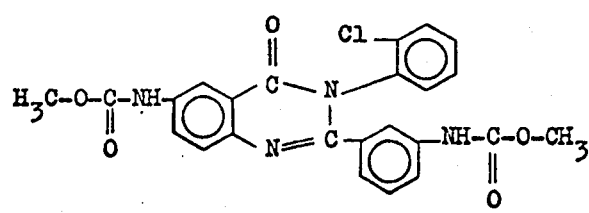
(8)
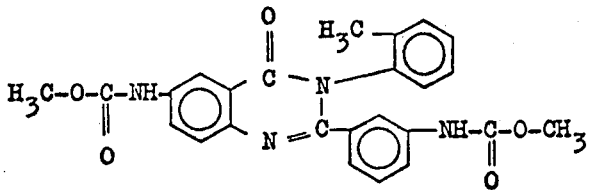

Table 1 (cont'd)
Compound No.    Formula
(9)
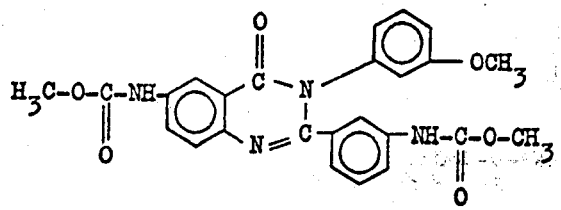
(10)
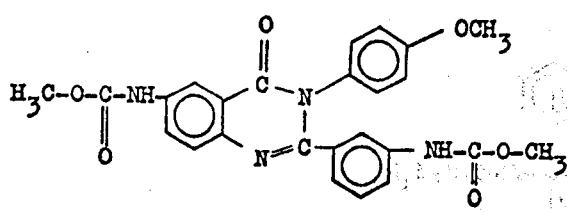
(11)
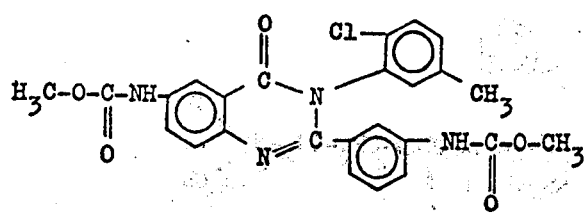
(12)
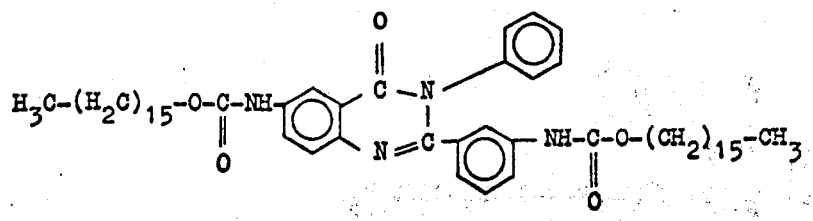
(13)
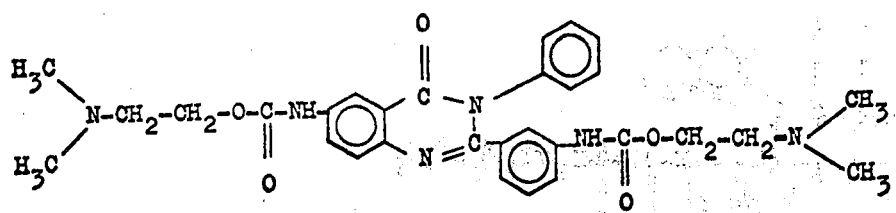

Table 1 (cont'd)
Compound No.           Formula
(14)
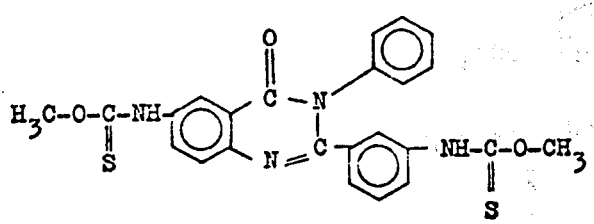
(15)
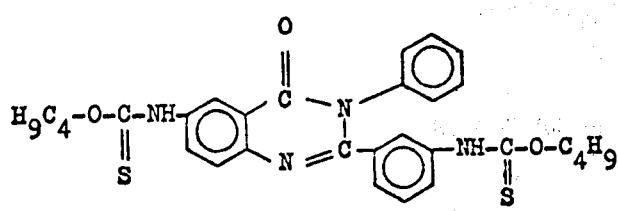
(16)
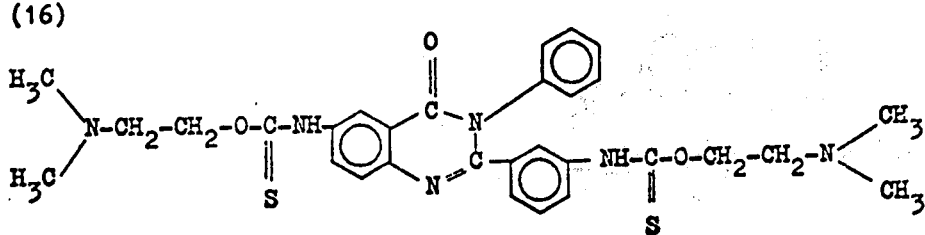
(17)
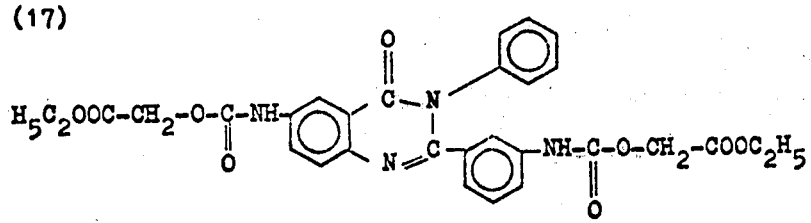
(18)
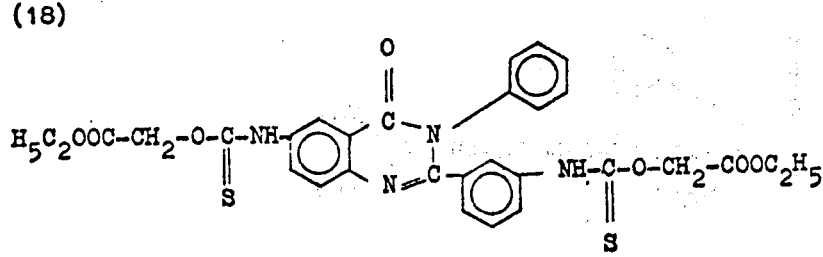

Table 1 (cont'd)

Compound No.　　　　　　　　　　Formula (19)

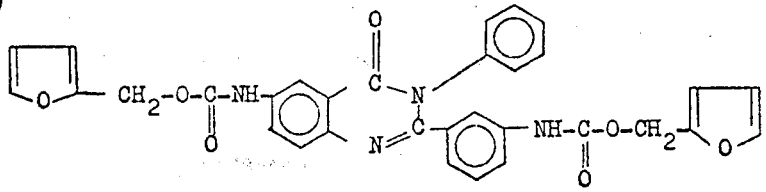

(20)

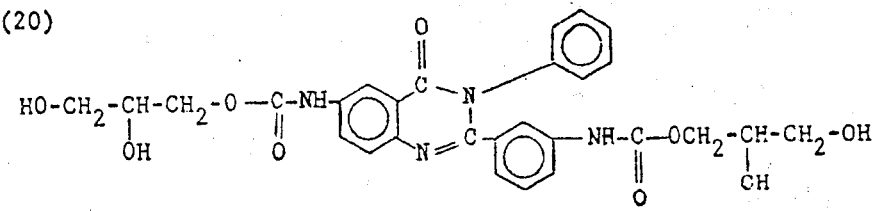

(21)

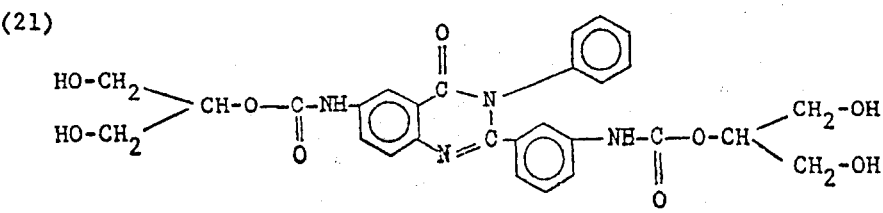

The following examples will serve to further typify the invention without being a limitation on the scope thereof. The relationship of parts by weight to parts by volume is as of the kilogram to liters or of the gram to milliliters.

EXAMPLE 1

2-[3'-(methoxycarbonylamino)-phenyl]-3-phenyl-6-methoxycarbonylamino-4-(3H)-quinazolone [Compound No. (2)]

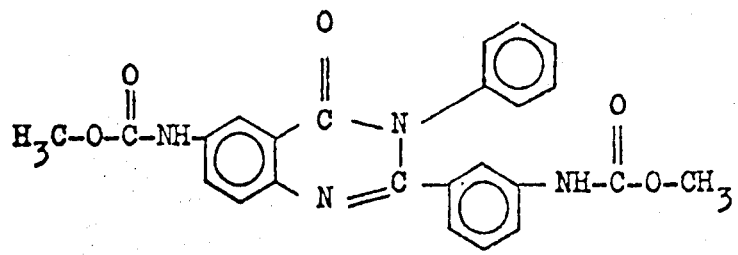

a. From 2-(3'-aminophenyl)-3-phenyl-6-amino-4-(3H)-quinazolone and chloroformic acid methyl ester.

32.8 parts by weight of 2-(3'-aminophenyl)-3-phenyl-6-amino-4-(3H)-quinazolone are dissolved in 150 parts by volume of N-methylpyrrolidone. 25 parts by weight of chloroformic acid methyl ester are added dropwise at 2°–5°C, whilst cooling with ice. The mixture is then stirred for a further 4 hours at room temperature and thereafter poured into water, and the product is filtered off and recrystallised from ethanol, with addition of active charcoal.

Yield of 2-[3'-(methoxycarbonylamino)-phenyl]-3-phenyl-6-methoxycarbonylamino-4-(3H)-quinazolone: 34 parts by weight (76.5% of theory).

Melting point: 248°–51°C.

The melting point very greatly depends on the crystallinity of the product; if the product is precipitated in an amorphous form the melting point can be up to 50°C lower, for example at 198°–200°C, even though, according to analysis and IR examinations, the product does not contain any impurities.

Analysis: Calculated: C —64.86%, H—4.54%, O—18.0%, N—12.61%. Found: C—64.8%, H—4.6%, O—18.4%, N—12.6%.

b. From 2-(3'-isocyanatophenyl)-3-phenyl-6-isocyanato-4-(3H)-quinazolone and methanol.

38 parts by weight of 2-(3'-isocyanatophenyl)-3-phenyl-6-isocyanato-4-(3H)-quinazolone and 2 parts by volume of triethylamine are heated with 200 parts by volume of methanol to the boil for 30 minutes. Thereafter the mixture is stirred into water and the product is recrystallised from ethanol. Yield of 2-[3'-(methoxycarbonylamino)-phenyl]-3-phenyl-6-methoxycarbonylamino-4-(3H)-quinazolone: 36 parts by weight (81% of theory).

Melting point: 243°–45°C.

Analysis: Calculated: C—64.86%, H—4.54%, O—18.0%, N—12.61%. Found: C—64.7%, H—4.7%, O—18.2%, N—12.8%.

2-(3'-Isocyanatophenyl)-3-phenyl-6-isocyanato-4-(3H)-quinazolone is obtained as follows from 2-(3'-aminophenyl)-3-phenyl-6-amino-4-(3H)-quinazolone:

164 parts by weight of 2-(3'-aminophenyl)-3-phenyl-6-amino-4-(3H)-quinazolone are suspended in 1,000 parts by volume of anhydrous chlorobenzene. Dry hydrogen chloride is passed into the suspension until at least the amount of hydrochloric acid gas required to form the dihydrochloride has been absorbed. Thereafter phosgene is passed in at 80°–100°C until a clear solution is produced. The mixture is then stirred for a further ½ hour at 100°C, nitrogen is then blown through, and the clear solution is concentrated in vacuo.

According to IR examinations, the white product which remains is pure 2-(3'-isocyanatophenyl)-3-phenyl-6-isocyanato-4-(3H)-quinazolone.

Melting point 153°–155°C.

The other diisocyanates to be employed as starting compounds can be obtained analogously.

EXAMPLES 2 – 12

The quinazolone-bisurethanes listed in Table 1 are obtained analogously to Example 1 (a) from the following diamines and ethyl chloroformate in Example 2, methyl chloroformate in Examples 3 through 11 and 4-tert.butylcyclohexyl chloroformate in Example 12:

| Example | Diamine |
|---|---|
| 2 | 2-(3-aminophenyl)-3-phenyl-6-amino-4(3H) quinazolone |
| 3 | 2-(3-aminophenyl)-3-(2-chlorophenyl-6-amino-4(3H) quinazolone |
| 4 | 2-(3-aminophenyl)-3-(4-methoxyphenyl)-6-amino-4(3H) quinazolone |
| 5 | 2-(3-aminophenyl)-3-(2-methylphenyl)-6-amino-4(3H) quinazolone |
| 6 | 2-(3-aminophenyl)-3-(3-methoxyphenyl)-6-amino-4(3H) quinazolone |
| 7 | 2-(3-aminophenyl)-3-(2-chloro-5-methylphenyl)-6-amino-4(3H) quinazolone |
| 8 | 2-(3-aminophenyl)-3-methyl-6-amino-4(3H) quinazolone |
| 9 | 2-(4-aminophenyl)-3-phenyl-6-amino-4(3H) quinazolone |
| 10 | 2-(3-aminophenyl)-3-phenyl-7-amino-4(3H) quinazolone |
| 11 | 2-(4-aminophenyl)-3-phenyl-7-amino-4(3H) quinazolone |
| 12 | 2-(3-aminophenyl)-3-phenyl-6-amino-4(3H) quinazolone |

TABLE 2

| Ex. | Formula | Compound No. | Melting Point (°C) | Yield, % of theory |
|---|---|---|---|---|
| 2. | 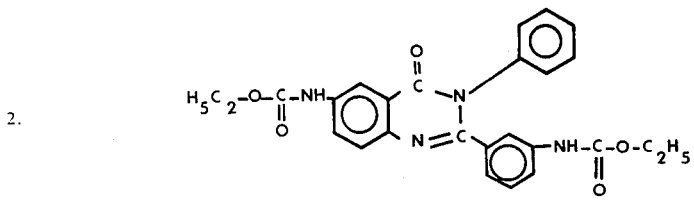 | (5) | 204–206 | 86 |

TABLE 2-continued

| Ex. | Formula | Compound No. | Melting Point (°C) | Yield, % of theory |
|---|---|---|---|---|
| 3. | [structure] | (7) | 250–53 | 72 |
| 4. | [structure] | (10) | 262–65 | 79 |
| 5. | [structure] | (8) | 252–54 | 71 |
| 6. | [structure] | (9) | 195–98 | 68 |
| 7. | [structure] | (11) | 166–70 | 76 |

TABLE 2-continued

| Ex. | Formula | Compound No. | Melting Point (°C) | Yield, % of theory |
|---|---|---|---|---|
| 8. | (structure) | (1) | 234-35 | 88 |
| 9. | (structure) | (3) | 266-68 | 72 |
| 10. | (structure) | (4) | 143-45 | 69 |
| 11. | (structure) | (22) | 267-70 | 67 |
| 12. | (structure) | (23) | 155-158 | 56 |

EXAMPLES 12 – 24

The quinazolonediurethanes listed in Table 3 are produced analogously to Example 1 (*b*) by substituting appropriate quantities of the following alcohols for methanol:

| Example | Alcohol |
|---|---|
| 13 | 2-dimethylaminoethanol |
| 14 | 2-dipropylaminoethanol |
| 15 | furfuryl alcohol |
| 16 | tetrahydrofurfuryl alcohol |
| 17 | benzyl alcohol |
| 18 | cyclohexanol |
| 19 | 2-phenoxyethanol |
| 20 | 2-pyrrolidinoethanol |
| 21 | 2-piperidinoethanol |
| 22 | 2-hexahydroazepinoethanol |
| 23 | 2-(1-imidazolyl)ethanol |
| 24 | 2-(1,2,4-triazol-2-yl)ethanol |

TABLE 3

| Example | Formula | Compound No. | Melting Point (°C) | Yield, % of theory |
|---|---|---|---|---|
| 13. | (structure) | (13) | 108-112 | 79 |
| 14. | (structure) | (24) | 126-129 | 64 |
| 15. | (structure) | (19) | 127-130 | 92 |
| 16. | (structure) | (25) | 189-200 | 99 |
| 17. | (structure) | (26) | 155-157 | 93 |
| 18. | (structure) | (27) | 145-150 | 99 |
| 19. | (structure) | (28) | 90-95 | 84 |
| 20. | (structure) | (29) | 161-164 | 50 |

TABLE 3 (Continuation)

| Example | Formula | Compound No. | Melting Point (°C) | Yield % of theory |
|---|---|---|---|---|
| 21. | | (30) | 175–178 | 96 |
| 22. | | (31) | 171–174 | 87 |
| 23. | | (32) | 146–150 | 95 |
| 24. | | (33) | 160–165 | 74 |

EXAMPLE 25

2-[3'-(β-hydroxyethoxycarbonylamino)-phenyl]-3-phenyl-6-(β-hydroxyethoxy-carbonylamino)-4-(3H)-quinazolone [Compound (6)].

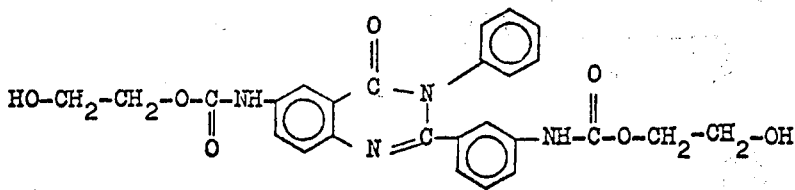

32.8 parts by weight of 2-(3'-aminophenyl)-3-phenyl-6-amino-4-(3H)-quinazolone and 100 parts by weight of glycol carbonate are heated to 100°C for 3 hours. After cooling, methanol is added, the mixture is cooled with ice, and the product is filtered off.

Yield of 2[3'-(β-hydroxyethoxycarbonylamino)-phenyl]-3-phenyl-6-(β-hydroxyethoxycarbonylamino)-4-(3H)-quinazolone: 26 parts by weight (53% of theory).

Melting point: 232°–235°C.

EXAMPLE 26

2-[3'-(β,γ-dihydroxypropyloxycarbonylamino)-phenyl]-3-phenyl-6-(β,γ-dihydroxypropyloxycarbonylamino)-4-(3H)-quinazolone [Compound No. 20].

13 parts by weight of 2-(3'-isocyanatophenyl)-3-phenyl-6-isocyanato-4-(3H)-quinazolone are dissolved in 60 parts by volume of anhydrous dimethylformamide. 60 parts by weight of glycerol, dissolved in 60 parts by volume of anhydrous dimethylformamide, and 5 parts by volume of triethylamine are then added. Thereafter the mixture is stirred for a further hour at room temperature and 4 hours at 60°C and is then stirred into water, and the product is filtered off and dried.

Yield of 2[3'-(β,γ-dihydroxypropyloxycarbonylamino)-phenyl]-3-phenyl-6-(β,γ-dihydroxypropyloxycarbonylamino)-4-(3H)-quinazolone: 15 parts by weight (67% of theory).

Melting point: 172°–74°C.

Analysis: Calculated: C—59.6%, H—4.96%, O—25.55%, N—9.95%. Found: C—59.1%, H—5.1%, O—24.9%, N—10.0%.

According to NMR examinations, the product only contains small amounts of the isomeric 2[3'-(bishydroxymethyl-methoxycarbonylamino)-phenyl]-3-phenyl-6-(bishydroxymethyl-methoxycarbonylamino)-4-

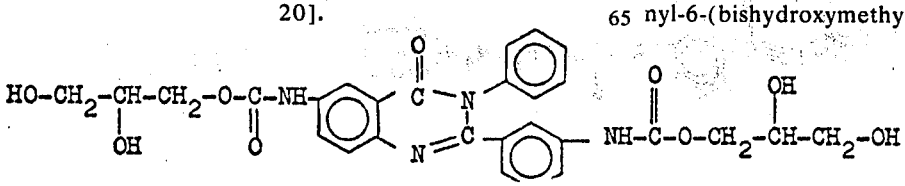

(3H)-quinazolone [Compound (21)] of the formula:

Melting point: 155°–158°C.

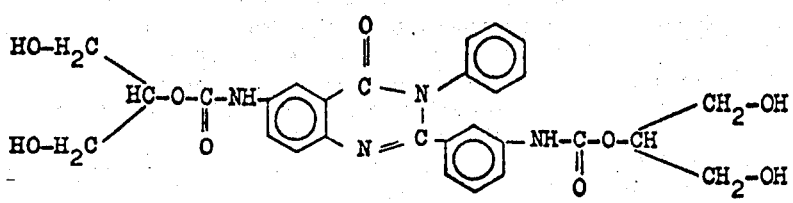

EXAMPLE 27

2-[3'-(methoxy-thiocarbonylamino)-phenyl]-3-phenyl-6-methoxythiocarbonyl-amino-4-(3H)-quinazolone [Compound (14)]

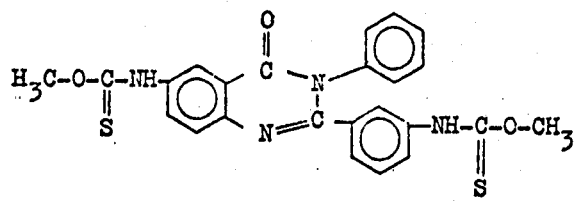

5 parts by weight of metallic sodium are dissolved in 150 parts by volume of absolute methanol. 34 parts by weight of 2-(3'-isothiocyanatophenyl)-3-phenyl-6-isothiocyanato-4-(3H)-quinazolone are then added and the mixture is stirred for a further 1½ hours at room temperature (about 20°C) and 1 hour at 40°C. The solution is filtered in order to remove small amounts of insoluble residues. The filtrate is stirred into water and acidified with hydrochloric acid. The precipitate is filtered off and dried in vacuo at 50°C.

Yield of 2-[3'-methoxy-thiocarbonylamino)-phenyl]-3-phenyl-6-methoxythiocarbonyl-amino-4-(3H)-quinazolone: 30.5 parts by weight (78% of theory).

Analysis: Calculated: C—60.5%, H—4.2%, O—10.1%, N—11.75%, S—13.4% Found: C—60.1%, H—4.5%, O—10.4%, N—12.0%, S—13.0%

The 2-(3'-isothiocyanatophenyl)-3-phenyl-6-isothiocyanato-4-(3H)-quinazolone employed as the starting material is produced as follows:

65.5 parts by weight of 2-(3'-aminophenyl)-3-phenyl-3-phenyl-6-amino-4-(3H)-quinazolone are introduced in portions, at 0.5°C, into a mixture of 240 parts by volume of water, 150 parts by volume of ethylene chloride, 60 parts by weight of calcium carbonate and 52 parts by weight of thiophosgene. Thereafter the mixture is stirred for a further 18 hours at room temperature. The product is then filtered off, stirred with dilute HCl, again filtered off and washed until neutral. and finally stirred with methanol and dried in vacuo.

Yield: 67 parts by weight (81.4% of theory).

The remaining diisothiocyanates to be employed as starting compounds can be obtained analogously.

EXAMPLES 28 – 29

The quinazolone-bisthiourethanes listed in Table 4 can be prepared analogously to Example 27 from 2-(3'-isothiocyanato)-3-phenyl-6-isothiocyanato-4-(3H)-quinazolone and sodium butoxide and sodium 2-dimethylaminoethoxide, respectively.

TABLE 4

| Example | Formula | Compound No. | Melting Point (°C) | Yield, % of theory |
|---|---|---|---|---|
| 28. | 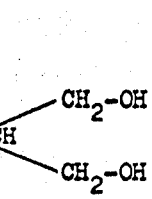 | (15) | 91–93 | 72.5 |
| 29. | | (16) | 128–136 | 87 |

The cytostatic activity of the compounds according to the invention can be conveniently observed in vivo in the model of transplanted lymphatic leukemia L 1210 on mice as follows: Mice weighing 18–22 g (Strain B 6 D 2 F 1) are injected intraperitoneally with $2 \times 10^5$ leukemia cells (L 1210) in 0.2 ml of ascites fluid. The test compound was administered intraperitoneally on each of four days, in an amount of from 25 to 700 mg/kg, starting 24 hours after the transplantation of the leukemia cells. The duration of the test is 2–3 weeks. To assess the results of the test, the survival time index (ST index) is determined as follows, using the Survival Time 50 (ST 50) of the control groups as 100%:

$$\text{ST index} = \frac{\text{ST 50 of the treated group} \times 100}{\text{ST 50 of the control group}}$$

The calculated quotient is the index of the change in the ST for animals under the treatment. Values less than 100% denote a reduced survival time of the treated group of animals and hence a toxic action of the preparation while values greater than 100% denote an increased survival time, which, depending upon the level of the index, express an inhibition of the tumor growth.

Table 5

| Compound No. | Leukaemia L 1210, optimum dose in mg/kg of body weight, 4 × intraperitoneally | Survival time index, % |
|---|---|---|
| (2) | 100 | 1047 |
| (3) | 200 | 113.3 |
| (5) | 350 | 913 |
| (7) | 100 | 187 |
| (8) | 700 | 187 |
| (11) | 175 | 126.7 |
| (31) | 25 | 113.3 |

As can be seen from the representative results given above, the quinazolone-diurethanes of the invention have highly valuable cytostatic properties. In actual use, these new quinazolonediurethanes can be administered orally or parenterally, through utilization of pharmaceutical compositions containing as the active ingredient at least one of these quinazolonediurethanes in admixture with a pharmaceutically acceptable solid or liquid diluent or carrier. In the present specification the expression "pharmaceutically acceptable diluent or carrier" denotes a non-toxic substance that when mixed with the active ingredient or ingredients renders it more suitable for administration. Other pharmaceutically acceptable ingredients such as salts in correct quantities to render the composition isotonic, buffers, surfactants, coloring and flavoring agents, and preservatives may of course also be present. Examples of suitable solid and liquid diluents and carriers include buffered aqueous solutions, isotonic saline aqueous solutions, paraffins such as petroleum fractions, vegetable oils such as groundnut and sesame oil, glycerol, glycols such as propylene glycol or polyethylene glycol optionally in admixture with water, natural rock powders as for example kaolins, aluminas, talc or chalk, synthetic rock powders such as highly disperse silica and silicates, sugars including unrefined sugar, lactose and glucose, starches, cellulose and its derivatives, stearates and stearic acid.

Examples of pharmaceutical compositions according to the invention are pastes, solutions, aqueous suspensions, elixirs, syrups, granules and powders, either free-flowing or compressed into tablets.

Pharmaceutical compositions of the invention adapted for oral administration employ diluents and carriers which adapt the active ingredient or ingredients for oral administration. Examples of such diluents and carriers include solid vehicles, excipients and lubricants such as glucose, lactose and sucrose, corn starch, potato starch, sodium carboxymethyl cellulose, ethyl cellulose and cellulose acetate, powdered gum tragacanth, gelatin, alginic acid, agar, stearic acid, sodium, calcium and magnesium stearates, sodium lauryl sulfate, polyvinyl-pyrrolidone, sodium citrate, calcium carbonate, and dicalcium phosphate.

The pharmaceutical compositions of the invention can also contain other non-toxic adjuvants and modifiers such as dyes, surfactants for example, emulsifiers, such as nonionic and anionic emulsifiers, for example polyoxyethylene-fatty acid esters, polyoxyethylene-fatty alcohol ethers, alkylsulfonates and arylsulfonates, and dispersing agents, for example lignin and methylcellulose, perfumes, flavoring agents, preservatives and biocides.

The quinazolonediurethanes of the invention may also be administered parenterally in pharmaceutical compositions adapted for parenteral injection. The diluents and carriers used are therefore preferably those that adapt the active ingredient for parenteral administration. Examples of such diluents and carriers are solvents and suspending diluents such as water and water-miscible organic solvents, in particular sesame oil, groundnut oil, aqueous propylene glycol, and N,N'-dimethyl formamide. Examples of pharmaceutical compositions of the invention are sterile isotonic saline aqueous solutions of the active ingredient, which may be buffered with a pharmaceutically acceptable buffer and are preferably pyrogen-free.

The pharmaceutical compositions of the invention preferably contain 0.1 to 99 wt.% more preferably 0.5 to 90 wt.% of a new quinazolonediurethane of the invention. Preferably the compositions are in dosage unit form. The expression "dosage unit form" as used in the present specification refers to a medicament in the form of discrete portions, each containing a unit dose or a multiple or sub-multiple of a unit dose of the active ingredient, as for example, one, two, three or four unit doses or a half, a third or a quarter of a unit dose. A "unit dose" is the amount of the active ingredient to be administered on one occasion and will usually be a daily dose, or a half, a third, or a quarter of a daily dose depending on whether the medicament is to be administered once or, for example, twice, three times, or four times a day. The discrete portions constituting the medicament in dosage unit form can include a protective envelope. The active ingredient can be undiluted and contained in such an envelope, or can be mixed with a pharmaceutically acceptable solid or liquid diluent or carrier. Such portions can for example be in monolithic coherent form, such as tablets, lozenges, pills, suppositories, or dragees; in wrapped or concealed form, the active ingredients being within a protective envelope, such as wrapped powders, cachets, sachets, capsules, or ampoules; or in the form of a sterile solution suitable for parenteral injection, such as ampoules of buffered, isotonic, sterile, pyrogen-free aqueous solution.

In general it has proved advantageous to administer amounts of 50 mg to 300 mg/kg of body weight per day to achieve effective results. Nevertheless it will at times be necessary to deviate from the amounts mentioned, and in particular to do so as a function of the nature and body weight of the subject to be treated, its individual behavior towards the medicine, the type of formulation and of administration of the medicine, and the point in time or interval at which it is administered. Thus it may in some cases suffice to use less than the above mentioned minimum amount, while in other cases the upper limit mentioned must be exceeded. Where larger amounts are administered, it can be advisable to divide these into several individual administrations over the course of the day.

The compounds can of course be administered in combination with other active ingredients.

What is claimed is:

1. A compound of the formula:

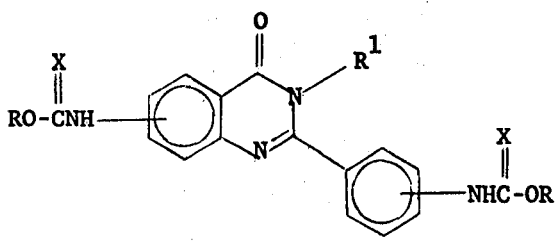

wherein
X is oxygen or sulfur;
R¹ is alkyl of 1 to 6 carbon atoms, unsubstituted phenyl or phenyl substituted with from one to three members selected from the group consisting of chloro, fluoro, bromo, alkyl of one to six carbon atoms and alkoxy of one to six carbon atoms; and
R is cycloalkyl of five or six carbon atoms, alkylcycloalkyl wherein alkyl is of one to six carbon atoms and cycloalkyl is of five or six carbon atoms, unsubstituted alkyl of one to 20 carbon atoms, or alkyl of one to six carbon atoms substituted by hydroxy, alkoxy of one to six carbon atoms, phenyl, phenoxy or cycloalkyl of five or six carbon atoms.

2. A compound according to claim 1 wherein R is cycloalkyl or (alkyl)cycloalkyl.

3. A compound according to claim 1 wherein R is unsubstituted alkyl of 1 to 6 carbon atoms or alkyl of one to six carbon atoms substituted by hydroxy, alkoxy of one to six carbon atoms, phenyl, phenoxy or cycloalkyl.

4. The compound according to claim 1 of the formula:

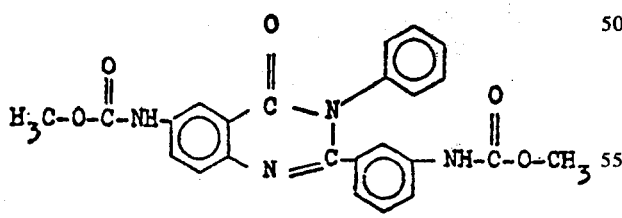

5. The compound according to claim 1 of the formula:

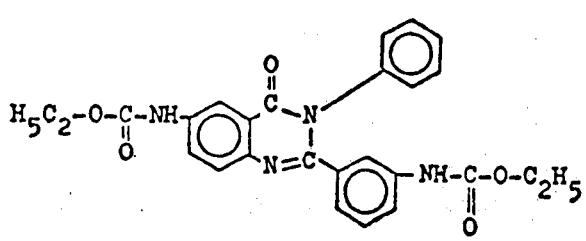

6. The compound according to claim 1 of the formula:

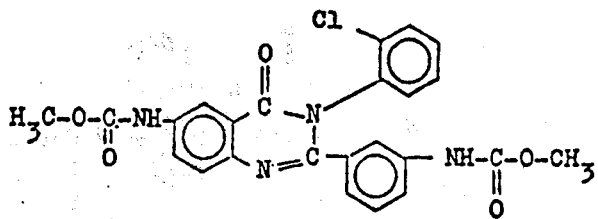

7. The compound according to claim 1 of the formula:

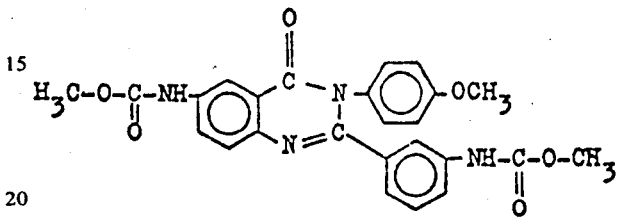

8. The compound according to claim 1 of the formula:

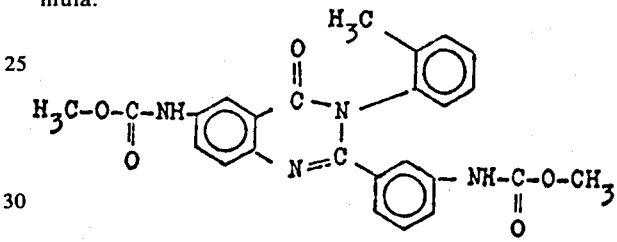

9. The compound according to claim 1 of the formula:

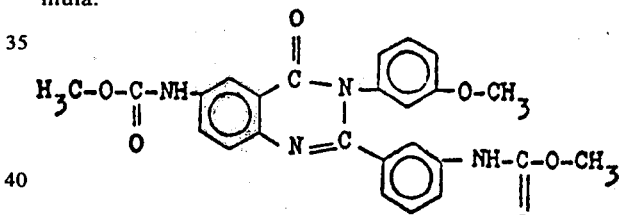

10. The compound according to claim 1 of the formula:

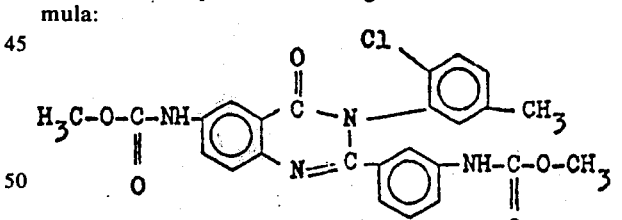

11. The compound according to claim 1 of the formula:

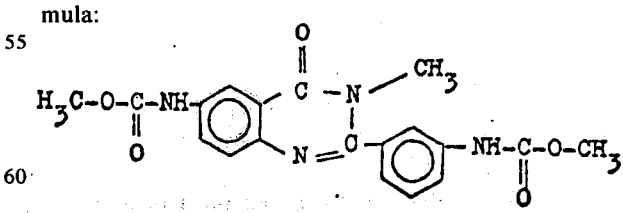

12. The compound according to claim 1 of the formula:

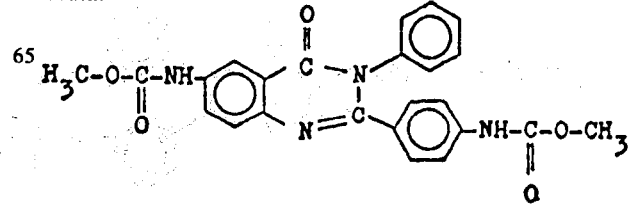

13. The compound according to claim 1 of the formula:

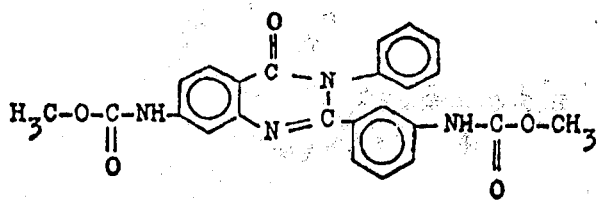

14. The compound according to claim 1 of the formula:

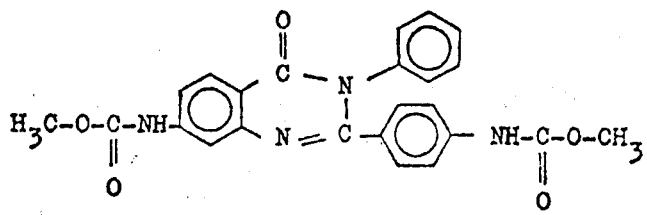

15. The compound according to claim 1 of the formula:

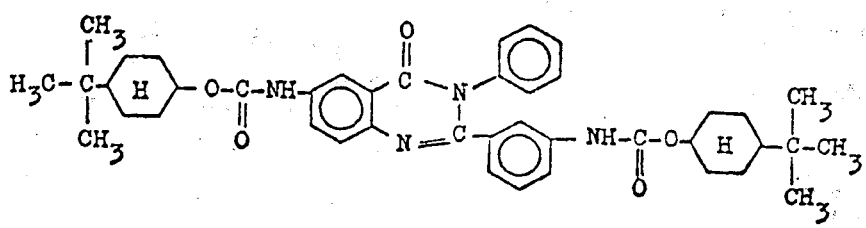

16. The compound according to claim 1 of the formula:

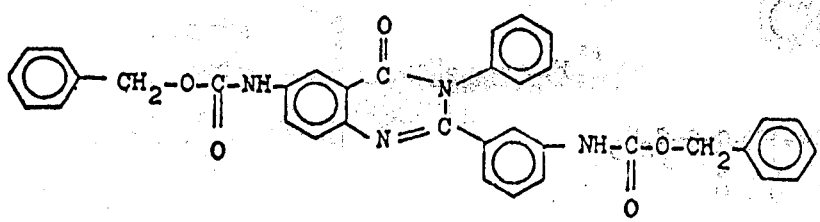

17. The compound according to claim 1 of the formula:

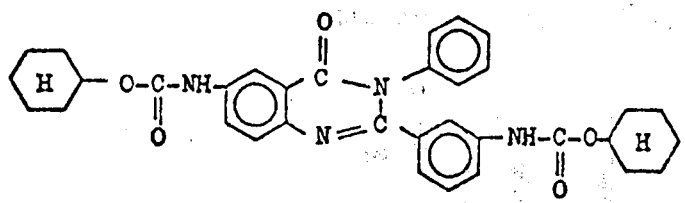

18. The compound according to claim 1 of the formula:

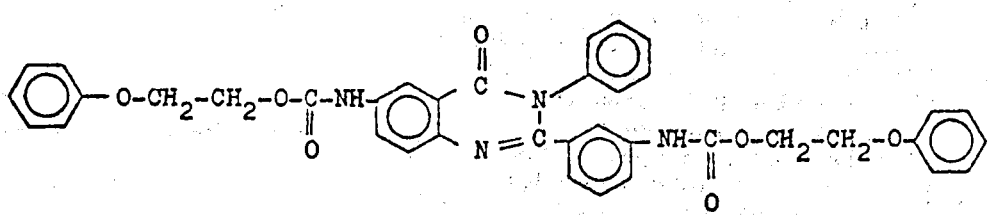

19. The compound according to claim 1 of the formula:

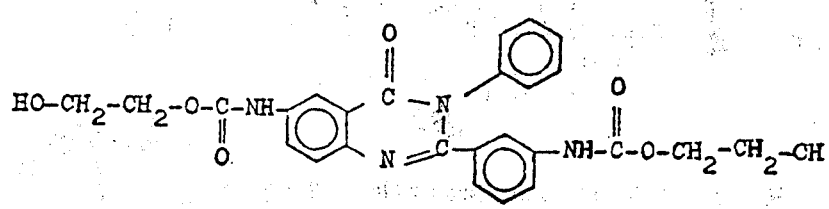

20. The compound according to claim 1 of the formula:

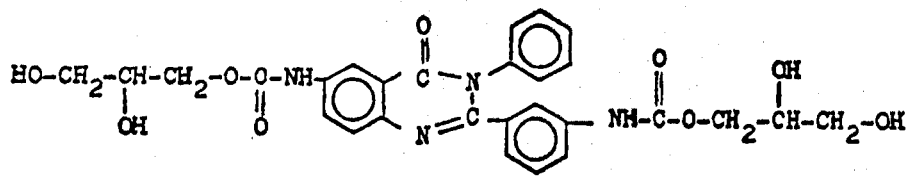
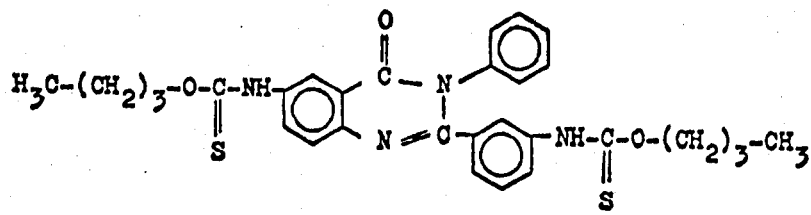
21. The compound according to claim 1 of the formula:
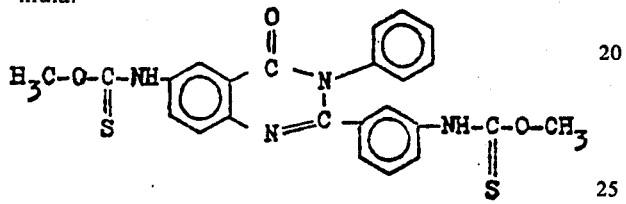
22. The compound according to claim 1 of the formula:
23. A compound according to claim 1 wherein
X is oxygen;
$R^1$ is phenyl or phenyl substituted by one or two members selected from the group consisting of chloro and alkyl of one to four carbon atoms; and
R is alkyl of one to six carbon atoms.
* * * * *